US008751268B1

(12) United States Patent
Reicher et al.

(10) Patent No.: US 8,751,268 B1
(45) Date of Patent: *Jun. 10, 2014

(54) SMART PLACEMENT RULES (71) Applicant: DR Systems, Inc., San Diego, CA (US)

(72) Inventors: Murray A. Reicher, Rancho Santa Fe, CA (US); Cole A. Genovese, Encinitas, CA (US); Carol G. Sloyer, La Jolla, CA (US); Thomas J. Edwards, San Diego, CA (US)

(73) Assignee: DR Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/907,128

(22) Filed: May 31, 2013

Related U.S. Application Data (63) Continuation of application No. 13/118,085, filed on May 27, 2011, now Pat. No. 8,457,990, which is a continuation of application No. 11/942,674, filed on Nov. 19, 2007, now Pat. No. 7,953,614.

(60) Provisional application No. 60/867,071, filed on Nov. 22, 2006.

(51) Int. Cl.
*G06Q 10/00* (2012.01)
*H04N 7/173* (2011.01)

(52) U.S. Cl.
USPC .................................................. 705/3; 705/2

(58) Field of Classification Search
USPC ............................................................ 705/3
See application file for complete search history.

(56) References Cited

U.S. PATENT DOCUMENTS

| 4,672,683 A | 6/1987 | Matsueda |
| 5,123,056 A | 6/1992 | Wilson |
| 5,179,651 A | 1/1993 | Taaffe et al. |
| 5,431,161 A | 7/1995 | Ryals et al. |
| 5,452,416 A | 9/1995 | Hilton et al. |
| 5,542,003 A | 7/1996 | Wofford |
| 5,734,915 A | 3/1998 | Roewer |
| 5,740,267 A | 4/1998 | Echerer et al. |

(Continued)

FOREIGN PATENT DOCUMENTS

WO    WO 2007/131157    11/2007

OTHER PUBLICATIONS

US 7,801,341, 9/2010, Fram et al. (withdrawn).
US 8,208,705, 6/2012, Reicher et al. (withdrawn).

(Continued)

*Primary Examiner* — Hiep V Nguyen
(74) *Attorney, Agent, or Firm* — Knobbe, Martens, Olson & Bear, LLP (57) ABSTRACT

A smart placement module determines components of received medial data, such as medical reports and image montages, to forward to one or more secondary location, such as an EMR system, based on smart placement rules that are established by a user that receives the medical data, such as a referring doctor. Thus, the smart placement module decreases or removes the need for the receiving user to manually select and transfer certain medical data for storage at the EMR system. Accordingly, the receiving user, and other authorized EMR system users, may have prompt access to the medical data via their respective connections to the EMR system. In one embodiment, the smart placement module transmits a patient identification file that is usable by the receiving EMR system to allow the EMR system to associate received medical data with other data regarding a respective patient.

28 Claims, 4 Drawing Sheets

(56) References Cited

U.S. PATENT DOCUMENTS

| | | |
|---|---|---|
| 5,779,634 A | 7/1998 | Ema et al. |
| 5,852,646 A | 12/1998 | Klotz et al. |
| 5,926,568 A | 7/1999 | Chaney et al. |
| 5,954,650 A | 9/1999 | Saito et al. |
| 5,976,088 A | 11/1999 | Urbano et al. |
| 5,986,662 A | 11/1999 | Argiro et al. |
| 5,987,345 A | 11/1999 | Engelmann et al. |
| 5,995,644 A | 11/1999 | Lai et al. |
| 6,115,486 A | 9/2000 | Cantoni |
| 6,128,002 A | 10/2000 | Leiper |
| 6,151,581 A | 11/2000 | Kraftson et al. |
| 6,175,643 B1 | 1/2001 | Lai et al. |
| 6,177,937 B1 | 1/2001 | Stockham et al. |
| 6,185,320 B1 | 2/2001 | Bick et al. |
| 6,243,095 B1 | 6/2001 | Shile et al. |
| 6,269,379 B1 | 7/2001 | Hiyama et al. |
| 6,304,667 B1 | 10/2001 | Reitano |
| 6,347,329 B1 | 2/2002 | Evans |
| 6,351,547 B1 | 2/2002 | Johnson et al. |
| 6,388,687 B1 | 5/2002 | Brackett et al. |
| 6,424,996 B1 | 7/2002 | Killcommons et al. |
| 6,438,533 B1 | 8/2002 | Spackman et al. |
| 6,463,169 B1 | 10/2002 | Ino et al. |
| 6,532,299 B1 | 3/2003 | Sachdeva et al. |
| 6,532,311 B1 | 3/2003 | Pritt |
| 6,556,695 B1 | 4/2003 | Packer et al. |
| 6,563,950 B1 | 5/2003 | Wiskott et al. |
| 6,574,629 B1 | 6/2003 | Kaufman et al. |
| 6,577,753 B2 | 6/2003 | Ogawa |
| 6,603,494 B1 | 8/2003 | Banks et al. |
| 6,606,171 B1 | 8/2003 | Renk et al. |
| 6,618,060 B1 | 9/2003 | Brackett |
| 6,630,937 B2 | 10/2003 | Kallergi et al. |
| 6,678,764 B2 | 1/2004 | Parvulescu et al. |
| 6,697,067 B1 | 2/2004 | Callahan et al. |
| 6,697,506 B1 | 2/2004 | Qian et al. |
| 6,734,880 B2 | 5/2004 | Chang et al. |
| 6,760,755 B1 | 7/2004 | Brackett |
| 6,775,402 B2 | 8/2004 | Bacus et al. |
| 6,778,689 B1 | 8/2004 | Aksit et al. |
| 6,820,100 B2 | 11/2004 | Funahashi |
| 6,829,377 B2 | 12/2004 | Milioto |
| 6,864,794 B2 | 3/2005 | Betz |
| 6,886,133 B2 | 4/2005 | Bailey et al. |
| 6,891,920 B1 | 5/2005 | Minyard et al. |
| 6,894,707 B2 | 5/2005 | Nemoto |
| 6,909,436 B1 | 6/2005 | Pianykh et al. |
| 6,909,795 B2 | 6/2005 | Tecotzky et al. |
| 6,917,696 B2 | 7/2005 | Soenksen |
| 6,996,205 B2 | 2/2006 | Capolunghi et al. |
| 7,016,952 B2 | 3/2006 | Mullen et al. |
| 7,022,073 B2 | 4/2006 | Fan et al. |
| 7,027,633 B2 | 4/2006 | Foran et al. |
| 7,031,846 B2 | 4/2006 | Kaushikkar et al. |
| 7,043,474 B2 | 5/2006 | Mojsilovic et al. |
| 7,050,620 B2 | 5/2006 | Heckman |
| 7,054,473 B1 | 5/2006 | Roehrig et al. |
| 7,058,901 B1 | 6/2006 | Hafey et al. |
| 7,092,572 B2 | 8/2006 | Huang et al. |
| 7,103,205 B2 | 9/2006 | Wang et al. |
| 7,106,479 B2 | 9/2006 | Roy et al. |
| 7,110,616 B2 | 9/2006 | Ditt et al. |
| 7,113,186 B2 | 9/2006 | Kim et al. |
| 7,139,416 B2 | 11/2006 | Vuylsteke |
| 7,149,334 B2 | 12/2006 | Dehmeshki |
| 7,155,043 B2 | 12/2006 | Daw |
| 7,162,623 B2 | 1/2007 | Yngvesson |
| 7,170,532 B2 | 1/2007 | Sako |
| 7,174,054 B2 | 2/2007 | Manber et al. |
| 7,209,149 B2 | 4/2007 | Jogo |
| 7,212,661 B2 | 5/2007 | Samara et al. |
| 7,218,763 B2 | 5/2007 | Belykh et al. |
| 7,224,852 B2 | 5/2007 | Lipton et al. |
| 7,260,249 B2 | 8/2007 | Smith |
| 7,263,710 B1 | 8/2007 | Hummel et al. |
| 7,272,610 B2 | 9/2007 | Torres |
| 7,346,199 B2 | 3/2008 | Pfaff |
| 7,366,992 B2 | 4/2008 | Thomas, III |
| 7,412,111 B2 | 8/2008 | Battle et al. |
| 7,450,747 B2 | 11/2008 | Jabri et al. |
| 7,526,114 B2 | 4/2009 | Seul et al. |
| 7,526,132 B2 | 4/2009 | Koenig |
| 7,545,965 B2 | 6/2009 | Suzuki et al. |
| 7,583,861 B2 | 9/2009 | Hanna et al. |
| 7,613,335 B2 | 11/2009 | McLennan et al. |
| 7,634,121 B2 | 12/2009 | Novatzky et al. |
| 7,636,413 B2 | 12/2009 | Toth |
| 7,660,488 B2 | 2/2010 | Reicher et al. |
| 7,668,352 B2 | 2/2010 | Tecotzky et al. |
| 7,683,909 B2 | 3/2010 | Takekoshi |
| 7,698,152 B2 | 4/2010 | Reid |
| 7,716,277 B2 | 5/2010 | Yamatake |
| 7,787,672 B2 | 8/2010 | Reicher et al. |
| 7,834,891 B2 | 11/2010 | Yarger et al. |
| 7,885,440 B2 | 2/2011 | Fram et al. |
| 7,920,152 B2 | 4/2011 | Fram et al. |
| 7,953,614 B1 | 5/2011 | Reicher |
| 7,970,625 B2 | 6/2011 | Reicher et al. |
| 8,019,138 B2 | 9/2011 | Reicher et al. |
| 8,046,044 B2 | 10/2011 | Stazzone et al. |
| 8,065,166 B2 | 11/2011 | Maresh et al. |
| 8,094,901 B1 | 1/2012 | Reicher et al. |
| 8,217,966 B2 | 7/2012 | Fram et al. |
| 8,244,014 B2 | 8/2012 | Reicher et al. |
| 8,292,811 B2 | 10/2012 | Relkuntwar et al. |
| 8,380,533 B2 | 2/2013 | Reicher et al. |
| 8,457,990 B1 | 6/2013 | Reicher et al. |
| 8,554,576 B1 | 10/2013 | Reicher et al. |
| 8,610,746 B2 | 12/2013 | Fram et al. |
| 2001/0016822 A1 | 8/2001 | Bessette |
| 2001/0042124 A1 | 11/2001 | Barron |
| 2002/0016718 A1 | 2/2002 | Rothschild et al. |
| 2002/0021828 A1 | 2/2002 | Papier et al. |
| 2002/0039084 A1 | 4/2002 | Yamaguchi |
| 2002/0044696 A1 | 4/2002 | Sirohey et al. |
| 2002/0073429 A1 | 6/2002 | Beane et al. |
| 2002/0091659 A1 | 7/2002 | Beaulieu et al. |
| 2002/0103673 A1 | 8/2002 | Atwood |
| 2002/0103827 A1 | 8/2002 | Sesek |
| 2002/0110285 A1 | 8/2002 | Wang et al. |
| 2002/0180883 A1 | 12/2002 | Tomizawa et al. |
| 2003/0005464 A1* | 1/2003 | Gropper et al. ............... 725/115 |
| 2003/0028402 A1 | 2/2003 | Ulrich et al. |
| 2003/0037054 A1 | 2/2003 | Dutta et al. |
| 2003/0065613 A1 | 4/2003 | Smith |
| 2003/0071829 A1 | 4/2003 | Bodicker et al. |
| 2003/0101291 A1 | 5/2003 | Mussack et al. |
| 2003/0115083 A1 | 6/2003 | Masarie et al. |
| 2003/0140141 A1 | 7/2003 | Mullen et al. |
| 2003/0164860 A1 | 9/2003 | Shen et al. |
| 2003/0187689 A1 | 10/2003 | Barnes et al. |
| 2003/0190062 A1 | 10/2003 | Noro et al. |
| 2003/0204420 A1 | 10/2003 | Wilkes et al. |
| 2003/0215122 A1 | 11/2003 | Tanaka |
| 2004/0024303 A1 | 2/2004 | Banks et al. |
| 2004/0086163 A1 | 5/2004 | Moriyama et al. |
| 2004/0088192 A1 | 5/2004 | Schmidt et al. |
| 2004/0105574 A1 | 6/2004 | Pfaff |
| 2004/0114714 A1 | 6/2004 | Minyard et al. |
| 2004/0143582 A1 | 7/2004 | Vu |
| 2004/0161164 A1 | 8/2004 | Dewaele |
| 2004/0165791 A1 | 8/2004 | Kaltanji |
| 2004/0190780 A1 | 9/2004 | Shiibashi et al. |
| 2004/0202387 A1 | 10/2004 | Yngvesson |
| 2004/0243435 A1 | 12/2004 | Williams |
| 2004/0252871 A1 | 12/2004 | Tecotzky et al. |
| 2004/0254816 A1 | 12/2004 | Myers |
| 2005/0027570 A1 | 2/2005 | Maier et al. |
| 2005/0043970 A1 | 2/2005 | Hsieh |
| 2005/0063575 A1 | 3/2005 | Ma et al. |
| 2005/0065424 A1 | 3/2005 | Shah et al. |
| 2005/0074157 A1 | 4/2005 | Thomas, III |
| 2005/0075544 A1 | 4/2005 | Shapiro et al. |
| 2005/0108058 A1 | 5/2005 | Weidner et al. |

(56) References Cited

U.S. PATENT DOCUMENTS

| | | | |
|---|---|---|---|
| 2005/0113681 | A1 | 5/2005 | DeFreitas et al. |
| 2005/0114178 | A1 | 5/2005 | Krishnamurthy et al. |
| 2005/0114179 | A1 | 5/2005 | Brackett et al. |
| 2005/0114283 | A1 | 5/2005 | Pearson et al. |
| 2005/0184988 | A1 | 8/2005 | Yanof et al. |
| 2005/0197860 | A1* | 9/2005 | Joffe et al. ............ 705/2 |
| 2005/0238218 | A1 | 10/2005 | Nakamura |
| 2005/0244041 | A1 | 11/2005 | Tecotzky et al. |
| 2005/0273009 | A1 | 12/2005 | Deischinger et al. |
| 2006/0008181 | A1 | 1/2006 | Takekoshi |
| 2006/0031097 | A1 | 2/2006 | Lipscher et al. |
| 2006/0058603 | A1 | 3/2006 | Dave et al. |
| 2006/0095426 | A1 | 5/2006 | Takachio et al. |
| 2006/0111941 | A1 | 5/2006 | Blom |
| 2006/0181548 | A1 | 8/2006 | Hafey et al. |
| 2006/0230072 | A1 | 10/2006 | Partovi et al. |
| 2006/0241979 | A1 | 10/2006 | Sato et al. |
| 2006/0277075 | A1 | 12/2006 | Salwan |
| 2006/0282408 | A1 | 12/2006 | Wisely et al. |
| 2007/0050701 | A1 | 3/2007 | El Emam et al. |
| 2007/0055550 | A1 | 3/2007 | Courtney et al. |
| 2007/0067124 | A1 | 3/2007 | Kimpe et al. |
| 2007/0073556 | A1 | 3/2007 | Lau et al. |
| 2007/0109402 | A1 | 5/2007 | Niwa |
| 2007/0124541 | A1 | 5/2007 | Lang et al. |
| 2007/0162308 | A1 | 7/2007 | Peters |
| 2007/0174079 | A1 | 7/2007 | Kraus |
| 2007/0192140 | A1 | 8/2007 | Gropper |
| 2007/0239481 | A1 | 10/2007 | DiSilvestro et al. |
| 2008/0059245 | A1 | 3/2008 | Sakaida et al. |
| 2008/0100612 | A1 | 5/2008 | Dastmalchi et al. |
| 2008/0103828 | A1 | 5/2008 | Squilla et al. |
| 2008/0275913 | A1 | 11/2008 | van Arragon et al. |
| 2009/0123052 | A1 | 5/2009 | Ruth et al. |
| 2009/0129643 | A1 | 5/2009 | Natanzon et al. |
| 2009/0198514 | A1 | 8/2009 | Rhodes |
| 2010/0198608 | A1 | 8/2010 | Kaboff et al. |
| 2010/0299157 | A1 | 11/2010 | Fram et al. |
| 2011/0016430 | A1 | 1/2011 | Fram |
| 2011/0316873 | A1 | 12/2011 | Reicher |
| 2012/0163684 | A1 | 6/2012 | Natanzon et al. |
| 2012/0194540 | A1 | 8/2012 | Reicher |
| 2013/0083023 | A1 | 4/2013 | Fram |
| 2013/0159019 | A1 | 6/2013 | Reicher |
| 2013/0169661 | A1 | 7/2013 | Reicher |

OTHER PUBLICATIONS

Crowley, Rebecca et al., Development of Visual Diagnostic Expertise in Pathology: an Information-processing Study, Jan. 2003, Journal of the American medical Informatics Association, vol. 10, No. 1, pp. 39-51.
Non-Final Office Action dated Aug. 28, 2007 in U.S. Appl. No. 11/179,384.
Final Office Action dated Jun. 26, 2008 in U.S. Appl. No. 11/179,384.
Non-Final Office Action dated Dec. 29, 2008 in U.S. Appl. No. 11/179,384.
Final Office Action dated Jul. 24, 2009, in U.S. Appl. No. 11/179,384.
Notice of Allowance dated Nov. 3, 2009, in U.S. Appl. No. 11/179,384.
Non-Final Office Action dated Aug. 18, 2010 in U.S. Appl. No. 12/702,976.
Interview Summary dated Dec. 1, 2010, in U.S. Appl. No. 12/702,976.
Final Office Action dated Feb. 17, 2011 in U.S. Appl. No. 12/702,976.
Interview Summary dated May 31, 2011 in U.S. Appl. No. 12/702,976.
Notice of Allowance dated Jul. 20, 2011, in U.S. Appl. No. 12/702,976.
Office Action dated Dec. 1, 2011, in U.S. Appl. No. 13/228,349.
Notice of Allowance dated Feb. 6, 2012, in U.S. Appl. No. 13/228,349.
Notice of Allowance dated Jul. 20, 2012, in U.S. Appl. No. 13/228,349.
Non-Final Office Action dated Oct. 1, 2009, in U.S. Appl. No. 11/268,261.
Notice of Allowance dated Feb. 2, 2010, in U.S. Appl. No. 11/268,261.
Interview Summary dated May 14, 2010, in U.S. Appl. No. 11/268,261.
Notice of Allowance dated May 17, 2010, in U.S. Appl. No. 11/268,261.
Supplemental Notice of Allowance dated Aug. 6, 2010, in U.S. Appl. No. 11/268,261.
Issue Notice dated Sep. 2, 2010, in U.S. Appl. No. 11/268,261.
Notice of Allowance dated Oct. 8, 2010, in U.S. Appl. No. 11/268,261.
Notice of Allowance dated Dec. 3, 2010, in U.S. Appl. No. 11/268,261.
Notice of Allowance dated Jan. 6, 2011, in U.S. Appl. No. 11/268,261.
Office Action dated May 16, 2011, in U.S. Appl. No. 12/857,915.
Interview Summary dated Sep. 6, 2011, in U.S. Appl. No. 12/857,915.
Final Office Action dated Dec. 15, 2011, in U.S. Appl. No. 12/857,915.
Office Action dated Jun. 12, 2012, in U.S. Appl. No. 12/857,915.
Non-Final Office Action dated May 13, 2009, in U.S. Appl. No. 11/265,979.
Final Office Action dated Dec. 22, 2009 in U.S. Appl. No. 11/265,979.
Non-Final Office Action dated Jul. 8, 2010 in U.S. Appl. No. 11/265,979.
Interview Summary dated Mar. 4, 2010 in U.S. Appl. No. 11/265,979.
Interview Summary dated Nov. 16, 2010 in U.S. Appl. No. 11/265,979.
Final Office Action dated Dec. 23, 2010 in U.S. Appl. No. 11/265,979.
Interview Summary dated Mar. 17, 2011 in U.S. Appl. No. 11/265,979.
Notice of Allowance dated May 26, 2011 in U.S. Appl. No. 11/265,979.
Office Action dated Jun. 8, 2012 in U.S. Appl. No. 13/171,081.
Interview Summary dated Jul. 31, 2012 in U.S. Appl. No. 13/171,081.
Final Office Action dated Oct. 12, 2012 in U.S. Appl. No. 13/171,081.
Interview Summary dated Nov. 6, 2012 in U.S. Appl. No. 13/171,081.
Non-Final Office Action dated Aug. 24, 2009 in U.S. Appl. No. 11/268,262.
Non-Final Office Action dated Apr. 16, 2010 in U.S. Appl. No. 11/268,262.
Interview Summary dated Nov. 24, 2009 in U.S. Appl. No. 11/268,262.
Interview Summary dated May 12, 2010 in U.S. Appl. No. 11/268,262.
Final Office Action dated Oct. 28, 2010 in U.S. Appl. No. 11/268,262.
Interview Summary dated Dec. 1, 2010 in U.S. Appl. No. 11/268,262.
Notice of Allowance dated Dec. 1, 2010 in U.S. Appl. No. 11/268,262.
Notice of Allowance dated Feb. 25, 2011 in U.S. Appl. No. 11/268,262.
Non-Final Office Action dated Jan. 11, 2012 in U.S. Appl. No. 13/079,597.
Notice of Allowance dated Apr. 25, 2012, in U.S. Appl. No. 13/079,597.
Non-Final Office Action dated Apr. 4, 2013 in U.S. Appl. No. 13/535,758.
Non-Final Office Action dated Jul. 27, 2009 in U.S. Appl. No. 11/265,978.
Notice of Allowance dated Nov. 19, 2009 in U.S. Appl. No. 11/265,978.
Notice of Allowance dated Apr. 19, 2010 in U.S. Appl. No. 11/265,978.

(56) References Cited

OTHER PUBLICATIONS

Supplemental Notice of Allowance dated May 3, 2010 in U.S. Appl. No. 11/265,978.
Supplemental Notice of Allowance dated Aug. 3, 2010 in U.S. Appl. No. 11/265,978.
Non-Final Office Action dated May 5, 2011 in U.S. Appl. No. 12/870,645.
Non-Final Office Action dated May 26, 2010 in U.S. Appl. No. 11/942,674.
Interview Summary dated Jul. 26, 2010 in U.S. Appl. No. 11/942,674.
Final Office Action dated Nov. 26, 2010 in U.S. Appl. No. 11/942,674.
Interview Summary dated Mar. 2, 2011 in U.S. Appl. No. 11/942,674.
Notice of Allowance, dated Apr. 1, 2011 in U.S. Appl. No. 11/942,674.
Non Final Office Action Dated Nov. 10, 2011 in U.S. Appl. No. 13/118,085.
Interview Summary, dated Feb. 17, 2012, in U.S. Appl. No. 13/118,085.
Final Office Action, dated Apr. 13, 2012, in U.S. Appl. No. 13/118,085.
Notice of Allowance, dated Feb. 6, 2013, in U.S. Appl. No. 13/118,085.
Non Final Office Action dated Sep. 16, 2010 in U.S. Appl. No. 11/942,687.
Interview Summary dated Dec. 3, 2010 in U.S. Appl. No. 11/942,687.
Final Office Action, dated Apr. 5, 2011 in U.S. Appl. No. 11/942,687.
Non-Final Office Action dated Apr. 14, 2010 in U.S. Appl. No. 11/944,027.
Interview Summary dated May 13, 2010 in U.S. Appl. No. 11/944,027.
Final Office Action dated Dec. 23, 2010 in U.S. Appl. No. 11/944,027.
Interview Summary dated Mar. 31, 2011 in U.S. Appl. No. 11/944,027).
Office Action dated Apr. 19, 2012 in U.S. Appl. No. 11/944,027.
Interview Summary dated Jun. 28, 2012 in U.S. Appl. No. 11/944,027.
Final Office Action dated Oct. 22, 2012 in U.S. Appl. No. 11/944,027.
Non-Final Office Action dated Sep. 29, 2010 in U.S. Appl. No. 11/944,000.
Final Office Action dated Apr. 20, 2011 in U.S. Appl. No. 11/944,000.
Interview Summary dated Jun. 7, 2011 in U.S. Appl. No. 11/944,000.
Office Action dated Feb. 3, 2012 in U.S. Appl. No. 12/622,404.
Interview Summary dated May 8, 2012 in U.S. Appl. No. 12/622,404.
Final Office Action dated Aug. 6, 2012 in U.S. Appl. No. 12/622,404.
Notice of Allowance dated Oct. 15, 2012 in U.S. Appl. No. 12/622,404.
Office Action dated Mar. 4, 2013 in U.S. Appl. No. 12/891,543.
Interview Summary dated Apr. 5, 2013 in U.S. Appl. No. 12/891,543.
Mendelson, et al., "Informatics in Radiology—Image Exchange: IHE and the Evolution of Image Sharing," RadioGraphics, Nov.-Dec. 2008, vol. 28, No. 7.
Office Action dated Aug. 23, 2013, in U.S. Appl. No. 12/857,915.
Notice of Allowance, dated Sep. 4, 2013, in U.S. Appl. No. 13/171,081.
Notice of Allowance, dated Aug. 23, 2013, in U.S. Appl. No. 13/535,758.
Non-Final Office Action dated May 31, 2013, in U.S. Appl. No. 13/345,606.
Interview Summary dated Aug. 15, 2013, in U.S. Appl. No. 13/345,606.
Notice of Allowance dated Jun. 5, 2013 in U.S. Appl. No. 11/944,027.
Appeal Brief dated Mar. 4, 2013 in U.S. Appl. No. 11/944,000.
Examiner's Answer dated Jun. 26, 2013 in U.S. Appl. No. 11/944,000.

\* cited by examiner

```
Exam Receive Options-IIIS Central Server                                    [X]

☑ Schedule an automatic receive every [5  ⇕] minutes              [  OK    ]
  ☐ Receive exams upon login                                        [ Cancel ]
  ┌Exam Copy Parameters─────────────────────────────────────────────────────┐
  │ ┌Exam Components────────────────────────────────────────────────────┐   │
302│ │ ☑ Images    ☑ Montages   ☑ Voice Clips   ☑ Notes   ☐ Reports    │   │
  │ └───────────────────────────────────────────────────────────────────┘   │
  └─────────────────────────────────────────────────────────────────────────┘

┌Receivable Exam Criteria─────────────────────────────────────────────────┐
  │ ☐ I am the Assigned Reading Physician                                   │
  │   ☐ [  Modality...    ] [                                           ]   │
  │   ☐ [ Acquisition Site...] [                                        ]   │
  │   ☑ [  Exam Status... ] [ Unread                                    ]   │
  │   ☐ [  Exam Priority... ] [                                         ]   │
  │   ☐ Additional Filter [                        ▼]                       │
  │   ☑ Ignore exams older than [ 2 weeks ▼]                                │
  │   ☐ Ignore exams performed from [7:00.00 AM ⇕] to [11:00.00 PM ⇕]       │
  │                                                                         │
  │   Maximum number of [ 3 ] exam(s) will be received automatically. (Doesn't apply to manual receive) │
  └─────────────────────────────────────────────────────────────────────────┘

┌After Exams Received─────────────────────────────────────────────────────┐
  │ ☑ Play sound [1 ⇕] Times  [                                ▶] Browse   │
  │ ☐ Launch program          [                                ▶] Browse   │
  └─────────────────────────────────────────────────────────────────────────┘

╭310                               ╭315
   [Copy Report to EMR] [Location:] [                           ] ▶ Browse
305│[Copy Montage > EMR] [Location:] [                           ] ▶ Browse
          ╰320                               ╰325
   [File Format    ] ☐[HL-7 Text]  ☐[PDF]    ☐[other...]
          ╰330        ╰332          ╰334       ╰336
```

FIG. 3

SMART PLACEMENT RULES

CROSS-REFERENCE TO RELATED APPLICATIONS

This application is a continuation of U.S. application Ser. No. 13/118,085, filed May 27, 2011, entitled "SMART PLACEMENT RULES, which is a continuation of U.S. application Ser. No. 11/942,674, filed Nov. 19, 2007, entitled "SMART PLACEMENT RULES," now U.S. Pat. No. 7,953, 614, which claims priority under 35 U.S.C. §119(e) to U.S. Provisional Application No. 60/867,071, filed Nov. 22, 2006, each of which are hereby expressly incorporated by reference in their entirety.

BACKGROUND OF THE INVENTION

1. Field of the Invention

The invention relates to the management and placement of medical data, and more particularly to the smart placement of received medical data within an Electronic Medical Records (EMR) system, for example.

2. Description of the Related Art

Medical data is increasingly being stored in the form of digital documents that can be electronically transmitted and shared between multiple computing devices. EMR systems store various types of medical data, such as images from x-rays and MRIs, montages of images, voice clips, notes, reports, and other text, audio, and/or video from a wide variety of sources. EMR systems receive medical data from physicians or other medical practitioners, for example, that have generated and/or received the medical data from one or more imaging facilities. This medical data often needs to be viewed, manipulated, interpreted, and/or shared between multiple medical members in the same facility or members in one or more distant facility. Accordingly, there is a need for improved systems and methods for the smart placement of medical records so that collaboration among medical faculty can take place.

SUMMARY OF THE INVENTION

In one embodiment, a method of managing medical data received from at least one medical imaging facility, the medical data comprising medical images and medical reports, comprises receiving data from a user indicating a first storage location of an EMR system for storing medical images and a second storage location of the EMR system for storing medical reports received from the imaging facilities, receiving medical images and medical reports from at least one of the medical imaging facilities via one or more networks, associating each of the received medical images and medical reports with respective patients, and transferring the medical images and the medical reports to the EMR system with information indicating the first and second storage locations for the respective medical images and medical reports.

In one embodiment, a method of manipulating medical data associated with a patient comprises receiving first information from a user of a first computer specifying medical data to be retrieved by the first computer, receiving instructions comprising an indication of a secondary storage location, receiving medical data associated with a patient in response to matching the first information to certain attributes associated with the medical data, and transferring at least some of the medical data to the secondary storage location, wherein the secondary storage location is configured to associate the transferred medical data with other medical data associated with the patient so that the transferred medical data is accessible by users of the secondary storage system.

In one embodiment, a medical data management system comprises a storage device for storing received medical data associated with a patient and for storing smart placement rules indicating one or more components of medical data to be transferred to an indicated secondary storage location, and a smart placement module for identifying one or more components of the received medical data that are indicated in the smart placement rules and forwarding a copy of the identified one or more components to the secondary storage location.

In one embodiment, a method of forwarding medical data to a patient records system, the method comprises receiving rules from a user of a computing system, the rules comprising criteria indicating which components of the medical data should be transmitted from a medical image storage device to the computing system and/or when the components should be transmitted to the computing system, receiving a storage location from the user of the computing system indicating where the medical data is to be stored in a patient records system, attaching information to medical data received from the medical image storage device, the information indicating one or more storage locations in the patient record system so that respective storage locations are associated with different components of the received medical data, and transmitting the received medical data and the attached information to the patient records system.

DETAILED DESCRIPTION OF THE CERTAIN EMBODIMENTS

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

As used herein, the terms "medical data," "medical-related data," and "medical records" are defined to include data in any format that is related to a patient. As non-limiting examples, the terms may include, but are not limited to, medical images, such as radiograph, computed tomography (CT), magnetic resonance imaging (MRI), Ultrasound (US), mammogram, positron emission tomography scan (PET), and nuclear scan (NM) images; montages of medical images; medical reports; voice clips, notes; and medical reports. Medical data may be stored in various formats, such as PDF, JPEG, GIF, PNG, DOC, XLS, PPT, MP3, WAV, HTML, XML, and various other formats.

A "component" of medical data is a category or type of medical data. For example, components of medical data may include an image component comprising medical images and a report component comprising a written report corresponding to the medical images. Components of medical data may include, for example, images, montages, voice clips, notes, and reports.

Figure 1A:
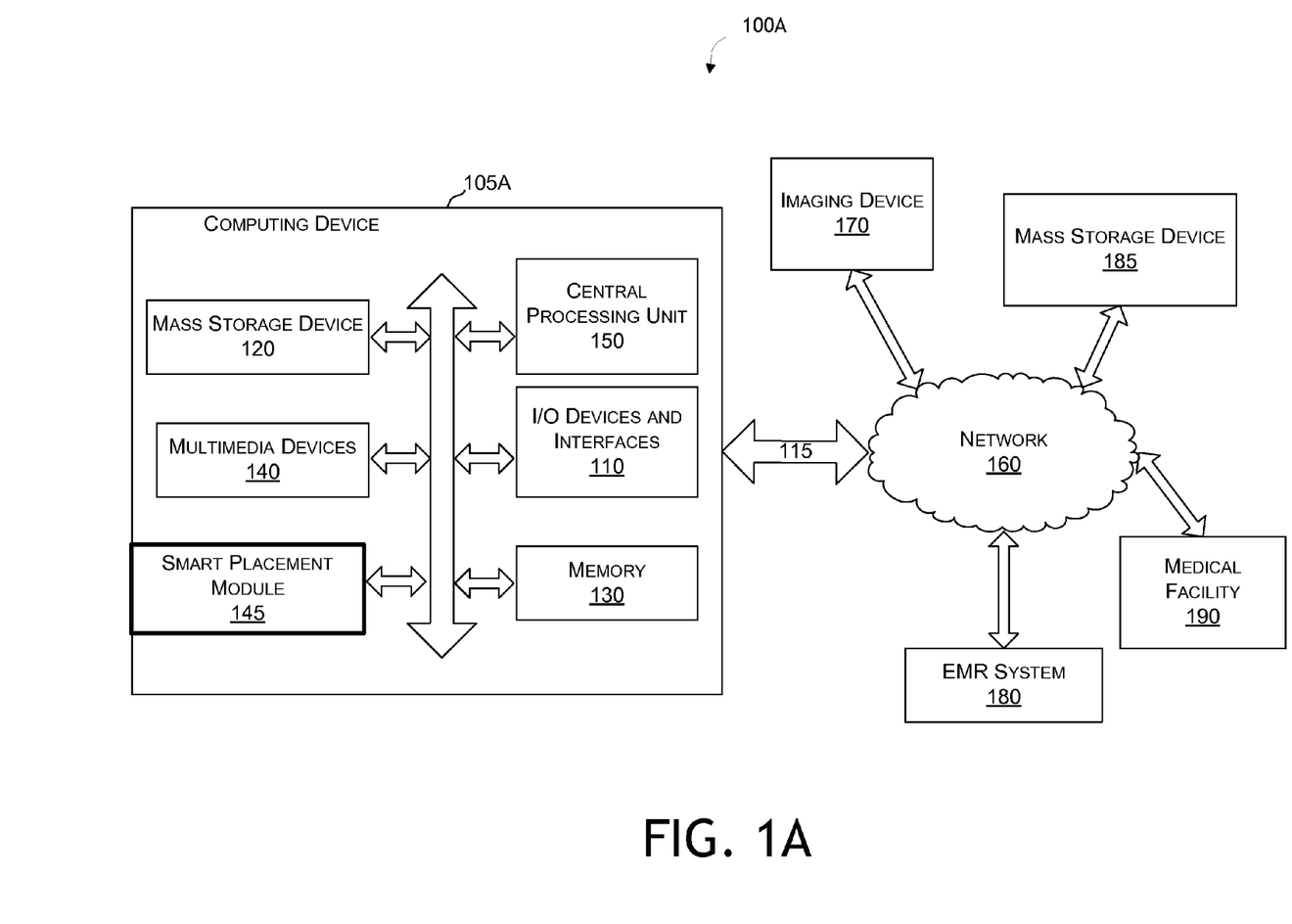
FIG. 1A is a block diagram of a computing system comprising a computing device in communication with a network and various networked devices.

FIG. 1A is a block diagram of a computing system 100A comprising a computing device 105A in communication with a network 160 and various networked devices. The computing system 100A may be used to implement certain systems and methods described herein. Depending on the embodiment, the functionality described below with reference to certain components and modules of the computing system 100A may be combined into fewer components and modules or further separated into additional components or modules.

The exemplary computing device 105 comprises a memory 130, such as random access memory ("RAM") for temporary storage of information and a read only memory ("ROM") for permanent storage of information, and a mass storage device 120, such as a hard drive, diskette, or optical media storage device. The mass storage device 120 may comprise one or more hard disk drive, optical drive, networked drive, or some combination of various digital storage systems. The computing device 105 also comprises a central processing unit (CPU) 150 for computation. Typically, the modules of the computing device 105 are in data communication via one or more standards-based bus system. In different embodiments of the present invention, the standards based bus system could be Peripheral Component Interconnect (PCI), Microchannel, SCSI, Industrial Standard Architecture (ISA) and Extended ISA (EISA) architectures, for example.

The computing device 105 is generally controlled and coordinated by operating system software, such as the Windows 95, 98, NT, 2000, XP, Vista, or other compatible operating systems. In Macintosh systems, the operating system may be any available operating system, such as Mac OS X. In other embodiments, the computing device 105 may be controlled by a proprietary operating system. Conventional operating systems control and schedule computer processes for execution, perform memory management, provide file system, networking, and I/O services, and provide a user interface, such as a graphical user interface ("GUI"), among other things.

The exemplary computing device 105A includes one or more of commonly available input/output (I/O) devices and interfaces 110, such as a keyboard, mouse, touchpad, and printer. In one embodiment, the I/O devices and interfaces 110 include one or more display devices, such as a monitor, that allows the visual presentation of data to a user. More particularly, display devices provide for the presentation of GUIs, application software data, and multimedia presentations, for example. According to the systems and methods described below, medical images may be stored on the computing device 105A and automatically transmitted to one or more EMR systems manipulated by the smart placement module 145 based on one or more placement rules established by a user of the computing device 105A. The computing device 105 may also include one or more multimedia devices 140, such as speakers, video cards, graphics accelerators, and microphones, for example.

In the embodiment of FIG. 1A, the I/O devices and interfaces 110 provide a communication interface to various external devices. In the embodiment of FIG. 1A, the computing device 105A is in data communication with a network 160, such as a LAN, WAN, or the Internet, for example, via a communication link 115. The network 160 may be coupled to various computing devices and/or other electronic devices. In the exemplary embodiment of FIG. 1A, the network 160 is in data communication with an imaging device 170, an Electronic Medical Record (EMR) system 180, a mass storage device 185, and a medical facility 190. Depending on the embodiment, the EMR system 180 may comprise proprietary medical record management software and/or one or more of various available third-party EMR systems. In addition to the devices that are illustrated in FIG. 1A, the network 160 may facilitate communications with other computing, imaging, and storage devices.

The imaging device 170 may be any type of device that is capable of acquiring medical images, such as MRI, x-ray, mammography, or CT scan systems. In one embodiment, the imaging device 170 is configured to store images and data associated with images. In one embodiment, the imaging device 170 communicates with the computing device 105 via the network 160, or one or more other wired and/or wireless networks, such as a secure LAN, for example. In one embodiment, the image data is stored in Digital Imaging and Communications in Medicine ("DICOM") format. The complete DICOM specifications, which may be found on the National Electrical Manufactures Association Website at <medical.nema.org>. Also, NEMA PS 3—Digital Imaging and Communications in Medicine, 2004 ed., Global Engineering Documents, Englewood Colo., 2004, is hereby incorporated by reference in its entirety.

The exemplary EMR system 180 is configured to store digital medical data so that doctors, medical staff, patients, and/or other authorized personnel can effectively view and share the medical data. The EMR system 180 may provide medical data from multiple sources to the computing device 105 via the network 160. Likewise, medical data from the computing device 105 may be provided to other medical facilities, such as the medical facility 190 of FIG. 1A, via the EMR system 180. Depending on the embodiment, the medical facility 190 may include one or more hospitals, clinics, doctor's offices, or any other facility that generates and/or processes medical data. The medical facility 190 may include one or more imaging devices, such as imaging devices that generate the image types described above in the definition of medical data. In one embodiment, multiple computing devices, such as the computing device 105, may be housed at the medical facility 190.

In the embodiment of FIG. 1A, the smart placement module 145 is configured to forward medical data received by the computing device 105A, such as from the imaging device 170 or the medical facility 190, to one or more EMR systems according to placement rules established by a user of the computing device 105. In one embodiment, medical data is received at the computing device 105 in response to matching of one or more auto-pull rules with particular medical data and/or components of the medical data. For example, in an auto-pull system, either the computing device 105 or a remote server may be configured to periodically select, based upon a user-defined schedule, medical data satisfying the user-specific rules. The user may be authenticated with the remote server in order to determine the user's rights to receive medical data and the selected medical data may then be transmitted to the computing device 105A so that it is locally available for the viewing physician, technician, or other authorized viewer. U.S. Pub. No. 2006/0095423, published on May 4, 2006 to Reicher et al. titled "Systems and Methods for Retrieval of Medical Data," which is hereby incorporated by reference in its entirety, describes various systems and methods for establishing auto-pull rules for selectively transferring medical data to a computing device.

In one embodiment, the smart placement module 145 determines components of received medial data to forward to one or more secondary storage locations, such as the EMR system 180 or a specific directory of a local storage device, based on smart placement rules that are established by an authorized user of the computing device 105. Although the description below refers primarily to an EMR system 180 as the secondary storage device, the systems and methods described herein are operable with any suitable secondary storage device, whether local or remote to the computing device 105.

Through the automatic application of smart placement rules by the smart placement module 145, the need for a user of the computing device 105 to manually select and transfer components of medical data to one or more secondary locations, such as the EMR system 180, is reduced or removed. Accordingly, the smart placement module 145 allows a user of the computing device 105, and other authorized computer users that are in communication with the EMR system 180, to locate data regarding a patient in the EMR system 180. In one embodiment, the smart placement module 145 provides an interface for an authorized user to establish smart placement rules that indicate what components of medical data should be forwarded to one or more secondary storage locations. In one embodiment, smart placement rules may also indicate storage locations for respective components of medical data, such as a directory on a local storage device, a directory on a shared storage device, or a folder in an EMR system, for example. Depending on the embodiment, the smart placement module 145 may be configured to copy the selected components of medical data (e.g., leaving a copy on the computing device 105) or to move the selected components of medical data (e.g., not leaving a copy on the computing device 105) to the selected secondary storage location. In one embodiment, the mass storage device 120 stores the user-specific rules. A further description of the smart placement module 145 and its processes will be discussed below.

Figure 1B:
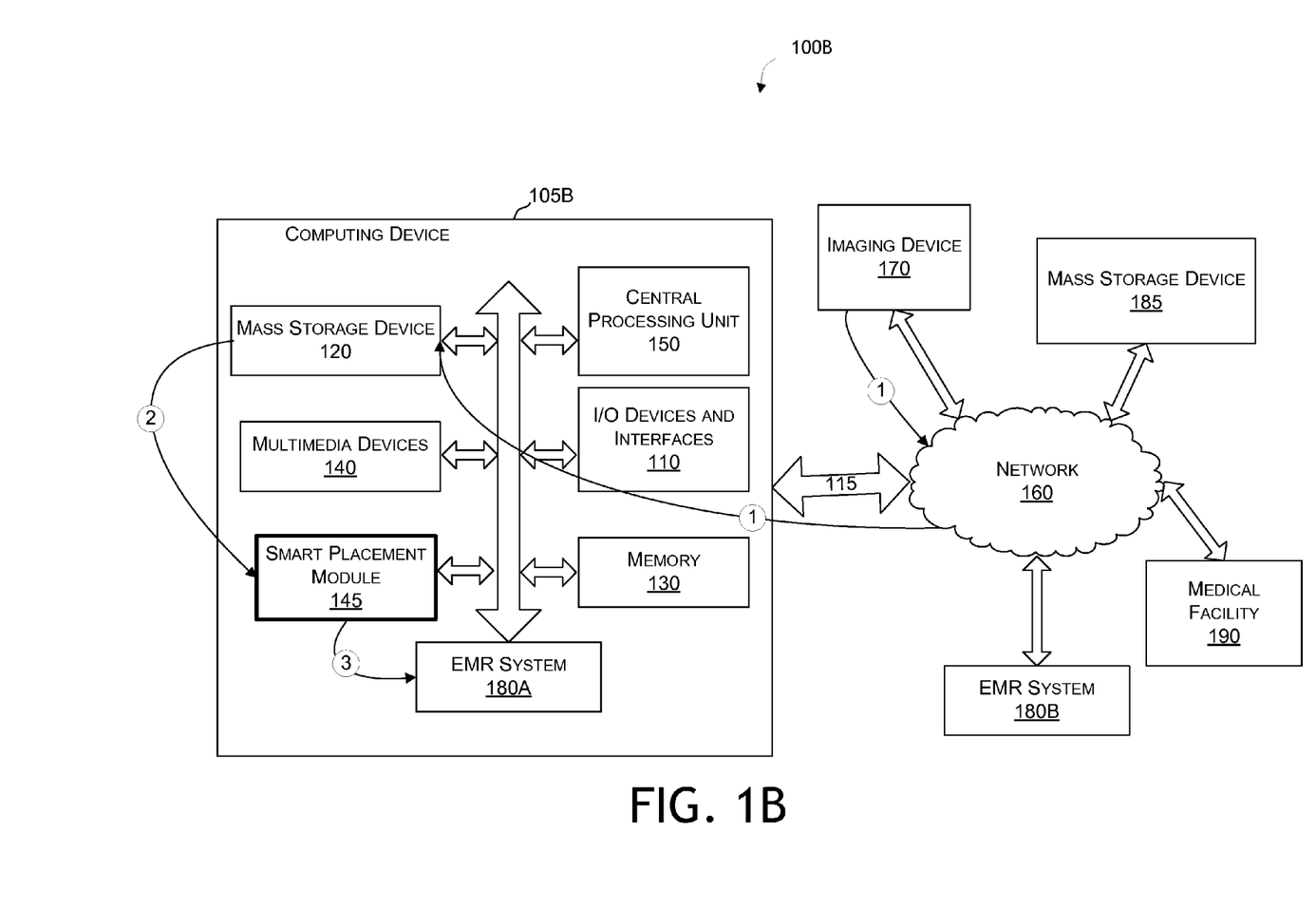
FIG. 1B is a block diagram illustrating one embodiment of a computing system comprising a computing device in communication with the imaging device via the network.

FIG. 1B is a block diagram illustrating one embodiment of a computing system 100B comprising a computing device 105B in communication with the imaging device 170 via the network 160. In the embodiment of FIG. 1B, the computing device 105B comprises a local version of the EMR system 180. In this embodiment, the EMR system 180 may be used exclusively by the computing device 105B, may be used by other devices coupled to the computing device 105B, such as via a secured local area network, and/or may be accessed by any authorized devices that are in communication with the network 160.

In the embodiment of FIG. 1B, an exemplary temporal flow of data is indicated by the circled numerals 1-3 and is described in further detail below. Depending on the embodiment, certain steps may be removed and additional steps may be added.

In step one of FIG. 1B, the imaging device 170 transmits medical data to the network 160, and the medical data, such as medical images, reports, and/or other medical information, is received and stored by the computing device 105B. In one embodiment, medical data is selected for transmission to the computing device 105B as a result of matching one or more auto-pull rules that are established by a user of the computing device 105B.

In step two, the smart placement module 145 of the computing device 105B applies smart placement rules to the received medical data. In one embodiment, the smart placement rules indicate that certain components of medical data is to be copied and/or moved to a secondary storage location either on the computing device 105B, such as in a folder of the EMR system 180, or to another device across the network 160. For example, smart placement rules may indicate that received medical data is to be transferred to a selected EMR system and associated with respective patient data on the EMR system.

In one embodiment, the smart placement rules indicate one or more components of medical data that are to be transmitted to a selected one or more destinations. For example, a user can establish placement rules indicating that only textual reports are to be transmitted to a selected EMR system, or the user can establish placement rules indicating that all components of received medical data should be transmitted to the selected EMR.

In step three of FIG. 1B, the indicated components of the received medical data are transmitted to the EMR system 180. In one embodiment, the transmitted components are associated with other medical data of the respective patient(s) at the EMR system 180. In such an embodiment, an authorized user of the EMR system 180 may access the transmitted components via the respective patient's inbox in the EMR system 180. Thus, in one embodiment the smart placement module 145 advantageously automates a process of selecting medical data for transmission to the EMR system 180 so that the medical data may be associated with other medical data associated with the patient at the EMR system 180. Additionally, the smart placement module 145 may be configured to automatically apply smart placement rules when medical data is received at the computing device 105 so that components of the medical data are quickly available to authorized users of the EMR system, without any intervention by the user.

In one embodiment, the smart placement module 145 generates a token comprising information indicating one or more software applications associated with components of medical data that are transmitted to the EMR system 180. In one embodiment, the smart placement module 145 determines the appropriate text, graphic, audio, etc., viewer(s) that may be used to present respective data items that are transmitted to the EMR system 180. For example, if the retrieved medical data includes image files, then the token sent by the smart placement module 145 to the EMR system 180 may indicate a specific third-party software viewing application that the viewing system should launch in order to view the image files. In one embodiment, the tokens may designate a class of software application so that the user's default application of a given type of application may be selected when indicated by a token.

In one embodiment, the smart placement module 145 generates a patient ID file that is transmitted with the indicated components to the EMR system 180. The patient ID file comprises an indication of a patient name, examination date, medical record number, and/or social security number, for example, of a patient associated with the transmitted medical data components. Thus, the patient ID file is usable by the EMR system 180 to place the medical data components in locations associated with the appropriate patient, such as folders, directories, or inboxes associated with respective patients. In other embodiments, the patient ID file may comprise additional information regarding a patient.

Figure 2:
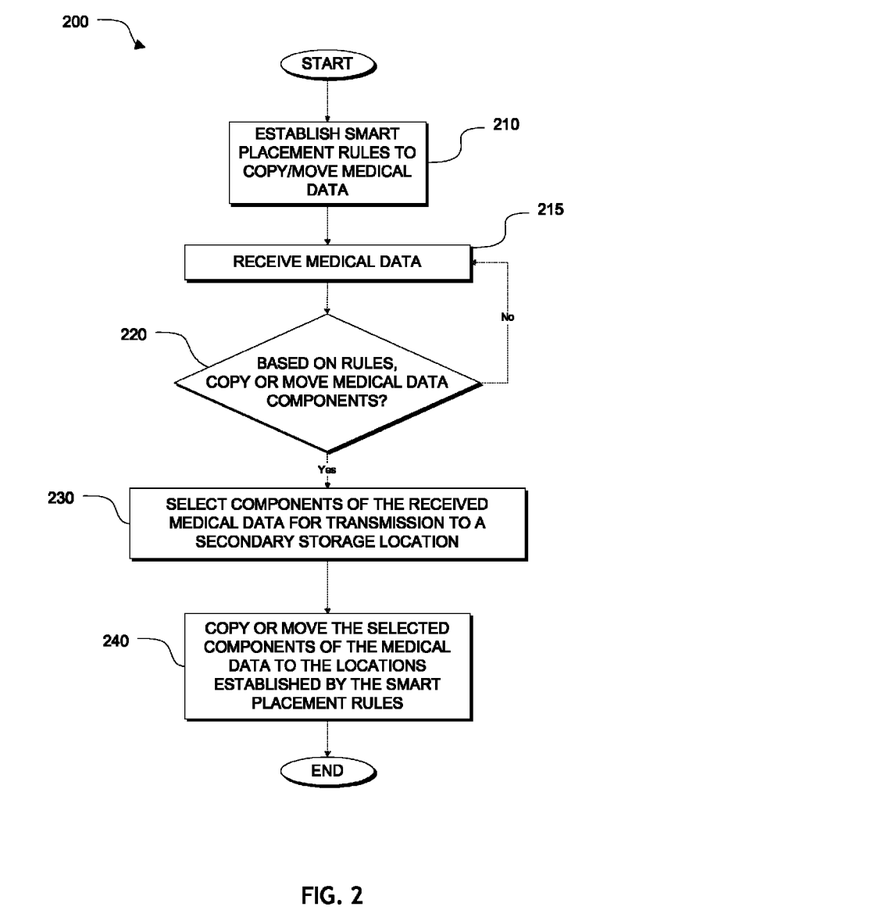
FIG. 2 is a flowchart illustrating one embodiment of a method of automatically forwarding received medical data to one or more predetermined locations based on smart placement rules.

FIG. 2 is a flowchart 200 illustrating one embodiment of a method of automatically forwarding received medical data to one or more predetermined locations based on smart placement rules. The method of FIG. 2A may be initiated in response to receiving new medical data at the computing device 105, such that the medical data is forwarded based on the smart placement rules substantially immediately after being received at the computing device 105. In other embodiments, the method of FIG. 2A is user initiated and may operate on medical data that has been stored on the computing devices or a networked device for an extended period of time. Depending on the embodiment, the flowchart of FIG. 2 may comprise fewer or more blocks and the blocks may be performed in a different order than illustrated.

Beginning in block 210, smart placement rules are established for movement or copying of medical data components to one or more secondary storage locations. In one embodiment, the smart placement rules comprise default system rules and/or user-specific rules for each user or group of users. Depending on the embodiment, the smart placement rules may include component criteria that must be matched by received medical data in order to trigger an associated smart placement action. For example, a smart placement rule may specify that only an image and report component of medical data is to be transmitted to a particular EMR system. Thus, when new medical data is received, only the image and report components are transmitted to the EMR system. In one embodiment, the smart placement rules indicated separate storage locations for respective medical data components, such as a first location for medical images and a second location for reports. Additionally, in some embodiments, the smart placement rules indicate a format that medical data components should be in prior to transferring to the EMR system, such as HL-7 text format, or PDF format, for example.

Figure 3:
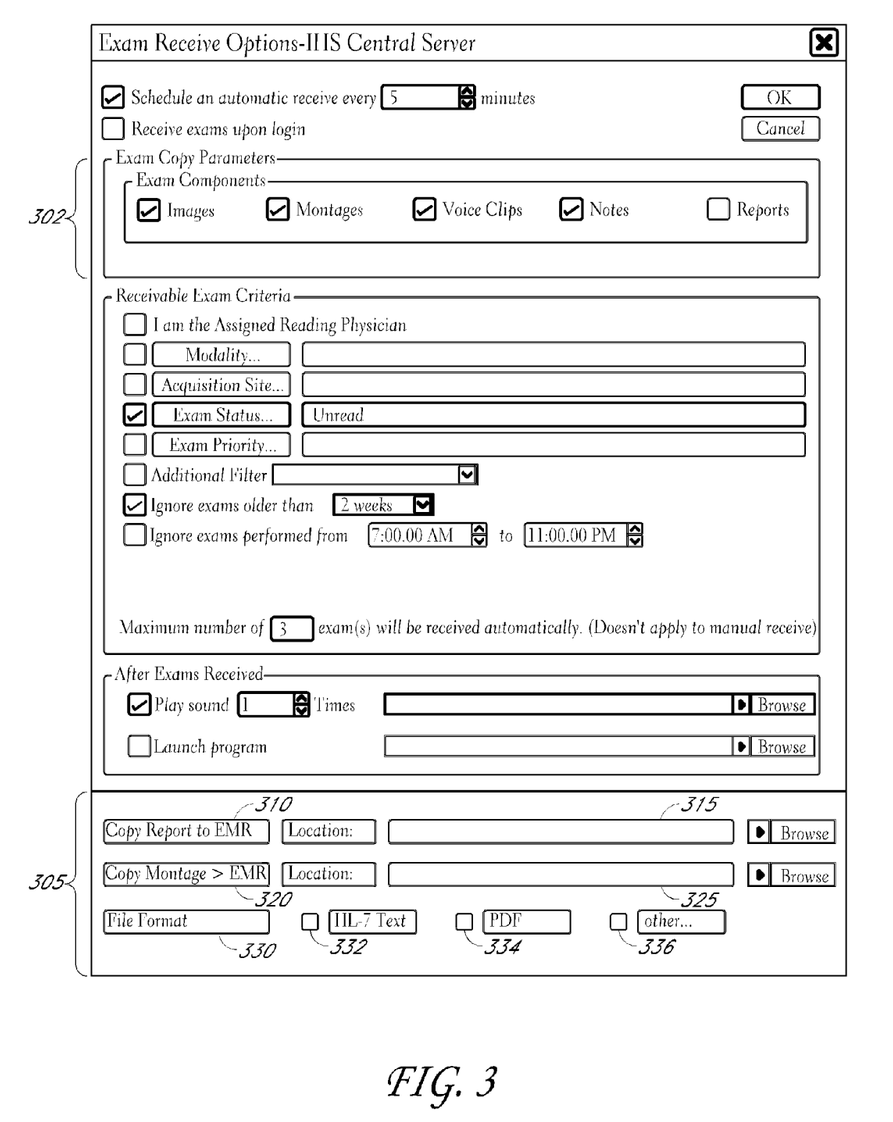
FIG. 3 is one embodiment of a graphical user interface that may be used to establish smart placement rules.

In one embodiment, the smart placement rules may also include criteria associated with header data of certain medical data components, such as time of day and/or date that a component is received by the computing device 105, a referring physician's name, a radiologist name, an exam type, an exam modality, and various other attributes of a components. In one embodiment, default system rules are applied to received medical data if user-specific rules have not been established. FIG. 3, which is described in further detail below, illustrates an exemplary user interfaces for establishing smart placement rules.

Moving to block 215, medical data is received at the computing device 105. As noted above, the medical data may be received from any suitable computing device that is in communication with the computing device 105, such as via the network 160. As defined above, the medical data may comprise one or more of multiple files of various formats and may include various information regarding a patient. In one embodiment, the medical data is stored in the mass storage system 120 of the computing device 105.

Next, in decision block 220 the computing device 105 applies the smart placement rules to the received medical data in order to determine which components of the medical data, if any, should be copied and/or moved to one or more local or remote secondary storage locations. If a smart placement rule matches one or more components of the medical data, the method continues to block 230. If no smart placement rules match with the medical data, the method returns to block 210 where medical data from another exam, another imaging source, and/or associated with another patient is received.

At block 230, the components of the medical data indicated by the placement rules are selected for transmission to the location indicated in the matching smart placement rule. As noted above, all components may be transmitted to a single location, e.g., a folder on a local or networked storage device or a local or networked EMR system, or the smart placement rules may indicate separate storage locations for respective components of the medical data.

Moving to block 240, the computing device 105 transmits the selected components to the location or locations associated with the matched smart placement rules. As noted above, in one embodiment a patient ID file indicating one or more attributes of the patient associated with the medical data components is also transmitted to the indicated secondary location. The patient ID file may be used, for example, by the EMR system in associating the transmitted medical data components with other medical data of respective patients. In this embodiment, the medical data of the patient is quickly made available to authorized users of the EMR system by accessing the patient's records stored by the EMR system.

In one embodiment, the smart placement module 145 generates one or more tokens that are associated with specific components of the transmitted medical data. The tokens comprise information regarding compatible and/or preferred software applications that may be launched in order to view and/or hear an associated medical data component. For example, if the selected medical data comprises a series of CT scan images, a token may be generated to indicate one or more software applications in which the CT images may be viewed. Likewise, a token indicating one or more software application in which a textual report may be viewed may be associated with a textual report component. In one embodiment, the EMR system 180 may display a link and/or icon associated with a token that may be selected by a user of the EMR system 180 in order to access the corresponding medical data in an appropriate software application. Certain tokens may comprise executable software code that launches a desired software application and opens selected medical data components in the software application. For example, an authorized user of the EMR system 180, such as a user of the computing device 105 or another computing device in communication with the network, may select a link associated with a token in order to invoke execution of the token, and subsequent launching of an indicated software application and opening of the corresponding medical data.

In one embodiment, the EMR system comprises separate patient inboxes wherein some or all of the patient's medical records are stored. In general, a patient's inbox is a location and/or index of locations where the patient's medical data is stored. This method may increase privacy of the medical data for specific patients by only allowing the patient, the patient's doctor, and/or other authorized users to access the patient's medical data.

FIG. 3 is one embodiment of a graphical user interface 300 that may be used to establish smart placement rules. Depending on the embodiment, the layout of the graphical user interface, the types of input fields, buttons, and checkboxes may be modified. The exemplary graphical user interface 300 comprises a component selection pane 302 that allows a user of the computing device 105, for example, to indicate which components of received medical data should be forwarded to one or more indicated secondary storage locations. In the embodiment of FIG. 3, check boxes for component types images, montages, voice clips, notes, and reports are provided, where a particular component is selected for transferring to an indicated secondary location if the corresponding checkbox is selected. In other embodiments, other controls may be used in order to allow a user to select one or more components. In other embodiments, fewer or additional components may be available for selection.

The exemplary user interface of FIG. 3 also comprises smart placement pane 305 that allow a user to select secondary storage locations for report and/or montage components of medical data. In the embodiment of FIG. 3, the smart placement pane 305 comprises a report copy button 310 that may be selected to indicate that received medical reports should be automatically transmitted to an EMR system, or other storage location, identified in field 315. Similarly, a montage copy button 320 may be selected in order to indicate that received montages should be automatically transmitted to an EMR system, or other storage location, identified in field 325.

In one embodiment, the smart placement module detects an EMR system that is used by the computing device and automatically populates fields 315, 325 with an indication of the detected EMR system(s). Where multiple EMR systems are detected, the text display fields 315, 325 may comprise dropdown fields that allow the user to select one or more of the EMR systems to which the medical data should be transmitted. In one embodiment, the user is provided with a directory structure that may be navigated in order to locate and select an EMR system or another storage location. In one embodiment, after establishing the smart placement rules, such as using the interface of FIG. 3, when medical data is received by the computing device 105, the components of the medical data indicated in the component selection pane 302 are automatically forward to the locations indicated in the smart placement pane 305.

The exemplary smart placement pane 305 further comprises buttons 332, 334, and 336 that allow the user to select a desired format for the medical data that is transmitted to the indicated EMR system. In the embodiment of FIG. 3A, HL-7 text format may be selected by selecting button 332 and PDF format may be selected by selecting button 334. In one embodiment, when button 332 is selected, medical data is converted into the Health Level 7 standard format, which is a widely known standard and format for medical records, before transmitting to the selected EMR system. Similarly, when button 334 is selected, medical data is converted into one or more Adobe PDFs before transmitting to the selected EMR system. The smart placement pane 305 further comprises an other button 336 that allows the user to select other formats for the medical data. In one embodiment, when the button 336 is selected, another user interface comprising additional data formats, such as DOC or RTF, for example, is presented to the user.

The foregoing description details certain embodiments of the invention. It will be appreciated, however, that no matter how detailed the foregoing appears in text, the invention can be practiced in many ways. For example, the above-described auto-retrieve may be performed on other types of images, in addition to medical images. For example, images of circuit boards, airplane wings, and satellite imagery may be analyzed using the described systems. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A computing system comprising:
one or more hardware computing devices configured to execute software instructions in order to at least:
receive medical data including medical data components;
access user-defined rules that indicate whether particular medical data components should be transmitted to a medical data storage system, and locations in the medical data storage system associated with particular medical data components; and
for each medical data component received that is determined to match a user-defined rule:
determine, based on the user defined rule, a location in the medical data storage system to store the medical data component; and
transmit to the medical data storage system the received medical data component and an indication of the determined location in the medical data storage system,
wherein the user-defined rules are provided by a user of the computing system.

2. The computing system of claim 1, wherein the medical data components include at least one of medical images, medical-related montages, medical-related reports, medical-related audio, or medical-related notes.

3. The computing system of claim 1, wherein the medical data storage system comprises an electronic medical records system, a storage device local to a user, or a storage device that is shared with multiple users.

4. The computing system of claim 1, wherein the determined location in the medical data storage system is associated with a patient indicated in the medical data component.

5. The computing system of claim 4, wherein the determined location comprises at least one of a folder, a directory, or an inbox.

6. A computing system comprising:
a storage device configured to store electronic software instructions;
one or more computer processors configured to execute the stored software instructions to cause the computing system to:
receive one or more medical data components; and
for each received medical data component:
determine a medical data component type associated with the medical data component;
access one or more user-defined rules associated with the medical data component type; and
in response to determining that the medical data component is not in a particular format indicated by the accessed user-defined rules, convert the medical data component to the particular format,
wherein the user-defined rules are provided by a user of the computing system and indicate particular formats for respective medical data component types.

7. The computing system of claim 6, wherein the particular format includes at least one of Health Level 7, Portable Document Format, DOC, RTF, XML, HTML, JPEG, GIF, PNG, XLS, PPT, MP3, or WAV.

8. The computing system of claim 6, wherein the one or more medical data components include at least one of images, montages, reports, audio, or notes.

9. A computing system comprising:
one or more hardware computer processors configured to execute instructions stored in an electronic storage device in order to at least:
receive medical data including items of medical data; and
for each received item of medical data, generate a token based on one or more attributes of the item of medical data, the token including an indication of one or more software applications suitable for viewing the item of medical data.

10. The computing system of claim 9, wherein the one or more hardware computer processors are further configured to execute instructions in order to at least:

for each received item of medical data, transmit the item of medical data and the generated token to a medical data storage system.

11. The computing system of claim 10, wherein the medical data storage system comprises an electronic medical records system, a storage device local to a user, or a storage device that is shared with multiple users.

12. The computing system of claim 10, wherein the item of medical data and the generated token are transmitted to a particular location in the medical data storage system.

13. The computing system of claim 12, wherein the particular location is determined based on one or more user-defined rules.

14. The computing system of claim 13, wherein the one or more user-defined rules further indicate whether the received item of medical data should be transmitted to the medical data storage system.

15. The computing system of claim 9, wherein the indication of one or more software application comprises an indication of a class of software applications.

16. The computing system of claim 9, wherein the token is generated automatically based on a determination that the one or more software applications are compatible with the item of medical data.

17. The computing system of claim 9, wherein the items of medical data include at least one of images, montages, reports, audio, or notes.

18. A computing system comprising:
one or more computing devices having one or more computer processors and configured to execute instructions in order to at least:
receive one or more items of medical data; and
for each received medical data item:
identify a patient associated with the medical data item;
generate a patient ID file including information associated with the identified patient;
associate the generated patient ID file with the medical data item; and
transmit the medical data item and the associated patient ID file to a same storage system.

19. The computing system of claim 18, wherein the generated patient ID file is useable to determine a particular location to store the medical data item.

20. The computing system of claim 18, wherein the generated patient ID file includes at least one of an indication of a patient name, an examination date, a medical record number, a social security number, or a patient specific identifier.

21. The computing system of claim 18, wherein the storage system comprises a medical data storage system.

22. The computing system of claim 21, wherein the medical data item is transmitted to a particular location in the medical data storage system based on information included in the generated patient ID file.

23. The computing system of claim 22, wherein the particular location is associated with the identified patient.

24. The computing system of claim 23, wherein one or more user-defined rules indicate whether the received medical data item should be transmitted to the medical data storage system.

25. The computing system of claim 22, wherein the particular location is associated with patient information and/or examination information associated with the medical data item.

26. A computing system comprising:
one or more computing devices configured to execute instructions in order to at least:
receive one or more electronic medical data items;
access rules that indicate locations in an electronic medical data storage system associated with particular patients; and
for each received medical data item:
identify a patient associated with the medical data item based on at least information included in one or more XML fields of the medical data item; and
based on the rules, transmit the medical data item to a location in the medical data storage system associated with the identified patient
wherein the rules include default system rules and/or rules provided by a user of the computing system.

27. The computing system of claim 26, wherein the patient associated with the medical data item is identified based on at least one of a patient ID, patient name, an examination date, a medical record number, a social security number, or a patient specific identifier included in the XML fields of the medical data item.

28. The computing system of claim 26, wherein the location is determined based on one or more of an identity of the patient, an examination date, an examination type, an examination modality, a medical procedure, and/or an ordering physician associated with the medical data item.

* * * * *